United States Patent
Flatt et al.

(10) Patent No.: US 6,954,071 B2
(45) Date of Patent: Oct. 11, 2005

(54) PIPELINE MAPPING AND INTERRUPTER THEREFOR

(75) Inventors: David William Flatt, South Wales (GB); Stephen John Petherick, Exeter (GB); Robert Ashworth Worsely, Worcester (GB)

(73) Assignee: Radiodetection Limited, Bristol (GB)

( * ) Notice: Subject to any disclaimer, the term of this patent is extended or adjusted under 35 U.S.C. 154(b) by 0 days.

(21) Appl. No.: 10/609,504

(22) Filed: Jul. 1, 2003

(65) Prior Publication Data

US 2004/0004479 A1 Jan. 8, 2004

Related U.S. Application Data

(62) Division of application No. 09/815,911, filed on Mar. 23, 2001, now Pat. No. 6,617,855.
(60) Provisional application No. 60/203,384, filed on May 11, 2000.

(30) Foreign Application Priority Data

Mar. 24, 2000 (GB) .......................................... 00072165

(51) Int. Cl.$^7$ ................................................ G01V 3/08
(52) U.S. Cl. ...................................................... 324/326
(58) Field of Search ................................ 324/326, 329, 324/220, 425, 72, 713, 263, 71.2, 551, 559; 702/64, 34, 33

(56) References Cited

U.S. PATENT DOCUMENTS

| | | |
|---|---|---|
| 4,356,444 A | 10/1982 | Saenz, Jr. |
| 4,387,337 A | 6/1983 | Beeman ........................ 324/52 |
| 4,542,344 A | 9/1985 | Darilek et al. .............. 324/326 |
| 5,077,486 A | 12/1991 | Marson et al. ................ 307/95 |
| 5,471,143 A | 11/1995 | Doany ......................... 324/326 |
| 6,107,811 A | 8/2000 | Caudill et al. .............. 324/713 |
| 6,127,827 A | 10/2000 | Lewis ......................... 324/326 |
| 6,141,701 A | 10/2000 | Whitney ........................ 710/5 |
| 6,211,807 B1 | 4/2001 | Wilkison ...................... 342/22 |
| 6,243,657 B1 | 6/2001 | Tuck et al. ................. 702/150 |
| 6,297,736 B1 | 10/2001 | Lewis et al. ................ 340/551 |
| 6,423,208 B1 * | 7/2002 | Russell ....................... 205/730 |
| 6,567,522 B1 * | 5/2003 | Blackburn .................. 379/413 |

FOREIGN PATENT DOCUMENTS

| | | |
|---|---|---|
| GB | 2245370 A | 12/1990 |
| JP | 070012950 | 1/1995 |
| WO | WO91/20002 | 6/1991 |

* cited by examiner

*Primary Examiner*—Jay Patidar
(74) *Attorney, Agent, or Firm*—Baker & Hostetler LLP

(57) ABSTRACT

Cathodic protection voltages are used to resist the damage to pipes or cables from electrolytic effects. However, localized fields can lead to stray currents and may result in corrosion and it is therefore desirable to detect and analyse those stray currents. Frequently there are several pipes in the area of interest and so it is necessary to distinguish between those pipes. Therefore the cathodic voltage on the pipes is modulated, with different pipes having different modulations. This modulation may be applied using an interrupter. Orthogonal modulations with non-unitary aspect ratios improve the discrimination between the pipes while maximizing the energy content of the modulation pattern. The analysis is improved when the interrupters are synchronized with each other and so repeating on the same time-base. This synchronization may be achieved using an external time signal such as GPS. An interrupter which can be used in this regard is also proposed, and may be powered from the cathodic voltage itself.

2 Claims, 6 Drawing Sheets

PIPELINE MAPPING AND INTERRUPTER THEREFOR

CROSS-REFERENCE TO RELATED APPLICATIONS

This application claims priority to and is a division of U.S. patent application entitled, PIPELINE MAPPING AND INTERRUPTER THEREFOR, filed Mar. 23, 2001, having Ser. No. 09/815,911, now U.S. Pat. No. 6,617,855, which claims the benefit of Provisional Application No. 60/203,384, filed May 11, 2000, the disclosure of which is hereby incorporated by reference.

BACKGROUND OF THE INVENTION

The present invention relates to the mapping of an underground cable or pipe. It also relate to an interrupter for interrupting the cathodic protection voltage applied to such an underground cable or pipe.

It is well known to apply a cathodic (negative) voltage to an underground cable or pipe (hereinafter "pipe") to reduce corrosion of that pipe. If the pipe is at a positive voltage relative to ground, electrolytic effects occur which damage the pipe. It should be noted that such cathodic protection voltage may be applied even when the pipe is coated to insulate it from the ground, because it is common for that insulation to develop holes or other faults which could result in localised damage.

However, it is also common for such pipes to experience electrical fields due to other objects such as adjacent pipes, or other electrical conductors such as railway lines, etc. Such localised fields sometimes result in the pipe experiencing a positive voltage relative to ground, so that corrosion occurs. It is therefore desirable to investigate currents in the pipe or cable to detect points where corrosion may occur. If stray currents are detected, these may be due to electric fields from other objects (such currents hereinafter being referred to as stray currents), appropriate action can be taken, such as repairing the fault or taking corrective action elsewhere by suitable voltage control, or even by providing sacrificial anodes at an adjacent fault.

In order to detect the stray currents, it is possible to make use of the magnetic fields generated by those currents, and detect those fields remotely from the pipe itself, such as at the surface. Detection of such magnetic fields is generally known, although special techniques may be needed because of the low magnitude of the currents.

There is also the problem that there may be several pipes in the area being investigated, and the currents from those other pipes may confuse the measurement.

SUMMARY OF THE INVENTION

Therefore, it is preferable that the cathodic protection voltage is modulated to enable the currents generated thereby to be more easily recognised by remote detectors. At its simplest, the modulation could be applied by a relay controlled switch connected between the pipe and the voltage source which supplies the cathodic protection voltage. However, the present invention, in its several aspects, seeks to develop stray current mapping arrangements, and also to provide an interrupter for applying a modulation to the cathodic protection voltage, and hence to the stray currents, and to improve the investigation of those stray currents.

Before discussing these aspects of the invention, however, it needs to be borne in mind that one source of stray currents is due to the cathodic protection voltage applied to other pipes which pass adjacent or across the pipe being investigated. Stray currents on the pipe being investigated may thus have multiple components, particularly when there are a large number of pipes adjacent each other.

Thus, a first aspect of the present invention proposes that the cathodic protection voltage of the pipe being investigated is modulated with a first modulation signal, and the cathodic protection voltage of a second pipe which passes adjacent the first pipe is modulated with a second modulation signal. Then, the stray currents on the pipe being investigated are analysed on the basis of the different modulation signals applied to the two pipes. If the stray currents are analysed at the first modulation, those current components due to the pipe itself, or due to other perturbations such as electric railways are determined. Then, if the stray currents are investigated at the second modulation, ie the modulation applied to another pipe, the effect of the linking between that other pipe and the pipe being investigated can be determined. This process can be repeated for multiple pipes by modulating with a distinct signal for each pipe.

Where the cathodic protection voltage of two pipes is to be modulated, whether it be the same modulation signal or with different modulation signals as in the first aspect, separate interrupters will be fitted to each pipe, and although the interrupters may be driven by oscillators having the same nominal frequency, manufacturing tolerances etc mean that synchronisation cannot be reliably achieved. Therefore, the interrupters need an additional system to provide synchronisation. The synchronisation represents a second aspect of the present invention.

Synchronisation could be achieved by directly connecting the two interrupters, so that the clock signal of one can be used as a reference against which the other is synchronised. However, in many situations, it is not practical for the interrupters connected to different pipes themselves to be connected. The pipes may only pass adjacent each other at a particular point along their length, and if the interrupters cannot be connected at that point, physical interconnection is problematic. Therefore, in a third aspect of the invention, synchronisation makes use of an arbitrary pre-set time for all interrupters. When any individual interrupter starts to operate, after it has stopped operating for some time, it determines the time interval between that pre-set time and the time of start of operation, and the interrupter signal (which is modulated by an appropriate modulation signal), is commenced at the point in the signal which corresponds to that which the signal would be if the signal had commenced at the pre-set time. In this way, the interrupters are synchronised as if any operating interrupter had started at the pre-set time, irrespective of the time which has past since that pre-set time.

In order for this operation to occur, the interrupter needs to determine the time between the pre-set time and the time at which the interrupter starts operation. If an absolute reference clock was available for each interrupter, that reference clock could be used. However, it is not normally economic to provide such accurate time measurement within an interrupter. Therefore, it is preferable that the interrupters make use of an external signal. If an external time signal is available (such as the Rugby signal in the UK), then that could be used. A further alternative is to make use of the Global Positioning System (GPS). Whilst those signals are primarily to provide positional information, they also provide a synchronised clock signal from which the interrupters can determine the time between the pre-set time and the time of starting the interrupter, and so can determine at which point in the interrupter signal the operation is to start.

To put this aspect another way; if all interrupters operated continually, synchronisation would be achieved by starting them all at the same time (the pre-set time). However, since the interrupters are to be turned on and off, a calculation is made whenever they are turned on to determine the point in the cycle they would have reached if they always had been turned on (from the pre-set time referred to above), and the signal is started at the appropriate time in the cycle corresponding to that which would have occurred if the interrupter had been on all the time.

Another aspect, which applies to the modulation of any single pipe, as well as modulations applied to multiple pipe as discussed above, is that the modulation is preferably an irregular modulation, rather than simple regular square-wave modulation. This makes the stray currents being investigated easier to distinguish from other currents in the vicinity of the pipe being investigated.

Since the currents on one pipe may be due not only to the modulation applied to that pipe, but also to the modulation applied to other pipes, it is important that the resulting field generated by the combinations of those modulations must be such that the individual modulations should be separately identifiable. It is possible to do this by modulating at different frequencies, but this has high power requirements. Therefore, in a further aspect of the present invention, it is proposed that the different pipes are modulated with signals which are a sequence of binary levels defining a bit pattern, with the bit pattern of each signal being orthogonal to all other patterns. Use of this aspect means that the presence of one pattern, and hence one signal, can accurately be determined and measured even in the presence of any or all of the other patterns and hence all other signals.

Orthogonality can be expressed mathematically as: $S1(t).S2(t)=0$ where S1 and S2 are the signal waveforms, represented as functions of time. The integral is taken over a period of time equal to the repeat period of the waveforms. If the equation holds true then the two signals $S1(t)$ and $S2(t)$ are orthogonal, provided neither signal is trivial, i.e. $S1^2(t)$ 0 and $S2^2(t)$ 0

Thus, this use of orthogonal signals represents a fourth aspect of the invention.

Even when the pipes are carrying orthogonal signals, erroneous results may be obtained if measurements are carried out in a location where two pipes are closely adjacent, since the signal in one pipe may couple to the other. When measurements are carried out remotely which seek to measure the modulation on one of those pipes, the same modulation may appear on the other pipe due to coupling, and therefore the magnetic field being measured will represent the sum of the fields from those two fields. Therefore, it is necessary to separate them.

To do this, it is proposed that one of the pipes be isolated and signals applied to it to determine its position. Then, after returning it to the non-isolated state, the net signals from the two pipes are investigated. Since the location of one of the pipes is known, it is then possible to determine the location of the other by subtracting the fields that would be generated by the pipe at the known location, and then analysing the resultant fields which then represent the second pipe. This subtraction process represents a fifth aspect of the invention.

Normally, in order to make for the use of the present invention, the interrupter includes a switch in the form of a solid-state device rather than a relay-controlled switch. It has been appreciated that it is then possible to make use of the cathodic protection voltage to provide power, instead of, or as a supplement to battery power. This represents a sixth aspect of the invention. In the sixth aspect, the interrupter has power storage (eg a capacitor) connected between the cathodic protection supply and ground. In the normal state, where the interrupter is not interrupting the cathodic protection voltage, a voltage is present across the power storage means which thus stores power which can be used to operate the interrupter when the interrupter is to function.

Indeed, this sixth aspect of the invention is not limited to the powering of an interrupter. Any suitable device connected to the pipe may thus be powered by the cathodic protection voltage.

As has been mentioned previously, the stray currents usually have small magnitudes, and therefore it is desirable to be able to detect those small currents remotely. To detect those currents, the detector apparatus disclosed in WO98/54601 may be used in which a plurality of sensors are provided, normally in a horizontally-extending array. Then, comparison of the sensor outputs enables the position of the pipe to be determined accurately. The sensors detect the magnetic fields generated by the currents, and the arrangements described in WO98/54601 permit detection even at low frequencies.

The final aspect of the present invention concerns the mapping of stray currents themselves. When an attempt is made to determine the position of an underground pipe using a detector with multiple sensors, the effect of an interfering adjacent pipe (a second pipe) is to distort the signals received by the sensors, so that it is not possible to determine from the signals from the sensors the location of the pipe being investigated (the first pipe).

Suppose now that a counter-interference is supplied to signals from the sensors, by modifying them as if there was an interfering pipe at a set location, and the current in that interfering pipe was varied. If this process is carried out until the outputs of the sensors are modified so as to coincide (or nearly so) at a particular point. Then, the "virtual" interference would have cancelled out the actual interference from the second pipe. At first sight, such cancellation would require the position of the virtual pipe to be set at the same place as the second pipe, but this turns out not to be the case. The effect of the second pipe at one location can be cancelled by a virtual pipe at another location, with a difference current. Thus, it is not necessary that the position of the virtual pipe is set accurately. Indeed, it could be present at some fixed location and sufficiently accurate results would normally be obtained. Of course, if the operator knew approximate the location of the second pipe, then greater accuracy could be achieved, but again the position needs only to be known approximately, not exactly, for sufficiently accurate results to be achieved. This use of a virtual interfering pipe to correct the distortions in sensor signals due to a real interfering pipe thus represents a seventh aspect of the invention.

BRIEF DESCRIPTION OF THE DRAWINGS

An embodiment of the present invention will now be described in detail, by way of example, with reference to the accompanying drawings, in which.

DETAILED DESCRIPTION OF THE INVENTION

Figure 1:
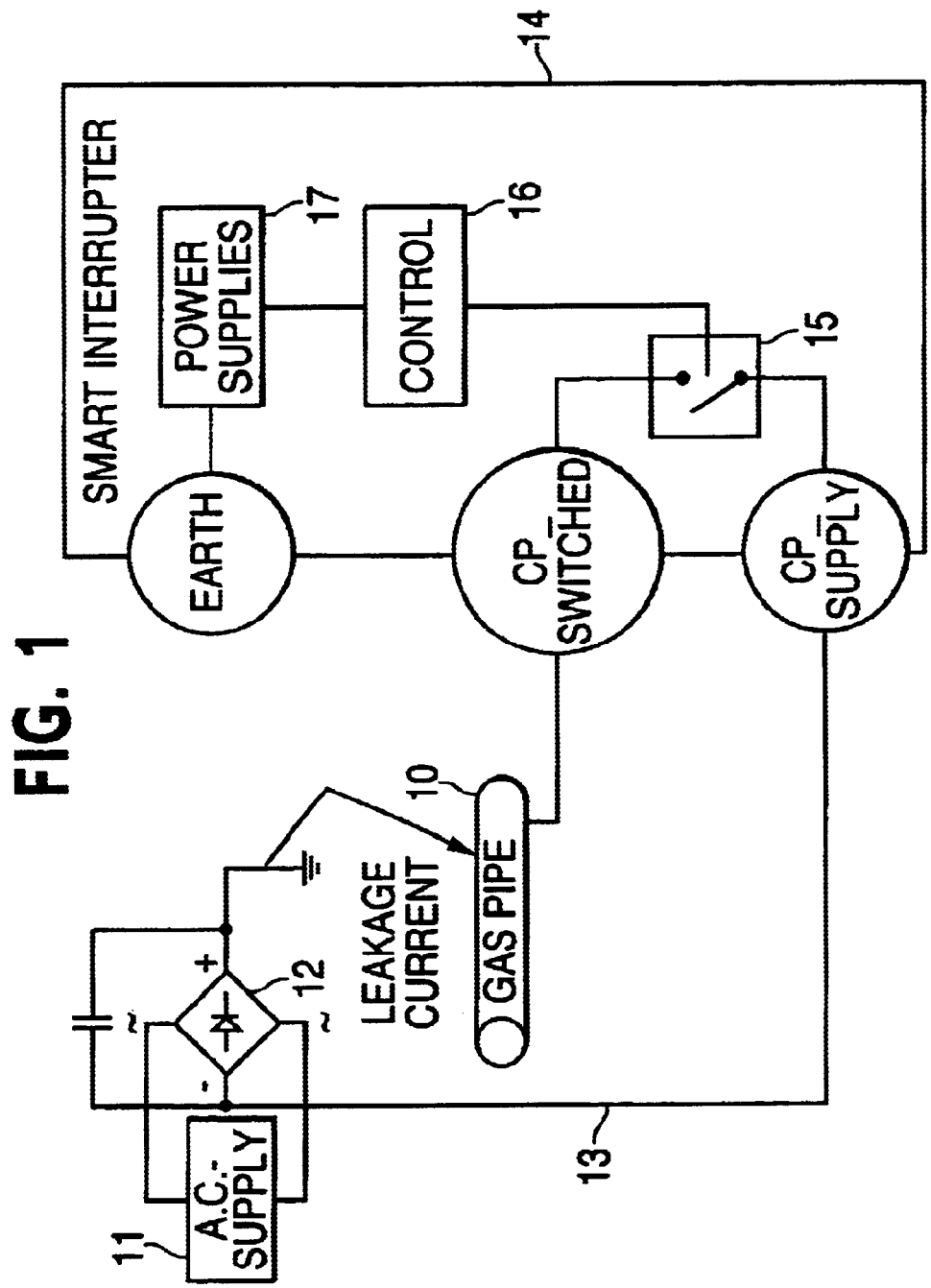
FIG. 1 is schematic diagram of a cathodic protection voltage system for a pipe line in which an interrupter according to present invention may be used.

Referring first to FIG. 1, a gas pipe 10 is to be protected against corrosion by having a cathodic (negative) protection voltage applied there too. That voltage is derived from a power supply 11, and rectified by a rectifier 12 so as to generate a cathodic voltage on a line 13 relative to ground. The line 13 is connected via an interrupter 14 to the pipe 10. The interrupter 14 comprises a switch 15 connected between the line 13 and the pipe 10, the switching of which is controlled by a control unit 16. The control unit 16 is powered from a power supply 17 within the interrupter 14, connected between the control unit 16 and ground.

Figure 2:
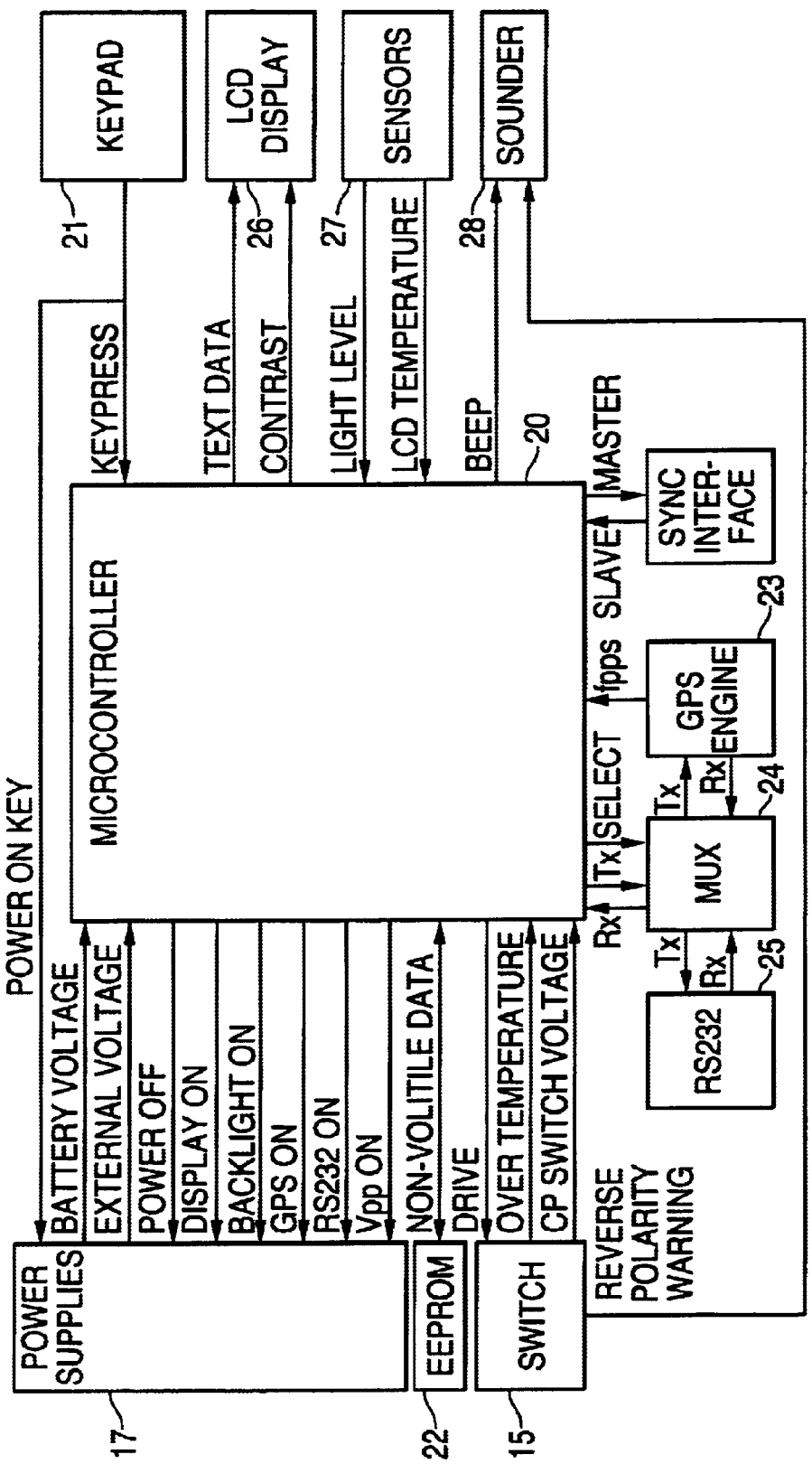
FIG. 2 shows the interrupter of FIG. 1 in more detail.

FIG. 2 shows the structure of the interrupter 14 in more detail. In FIG. 2, the switch 15 and the power supply 17 of FIG. 1 are shown as blocks, but all other components belong to the control unit 16. Thus, a microcontroller 20 is connected to the power supply 17 and to the switch 15. It is triggered by the action of a keypad 21 to cause it to operate, deriving data from a memory 22. The microcontroller 20 is also connected to a GPS device 23 which links via a multiplexor 24 and a suitable interface 25 to provide an independently synchronised signal at e.g. 1 pps to the microcontroller 20. The microcontroller 20 is also connected to a display unit 26 and to sensors 27 which sense temperature and light levels, control the display 26 and other components. A sounder 28 may be provided to provide a warning of faulty operation of the switch 15.

Figure 3:
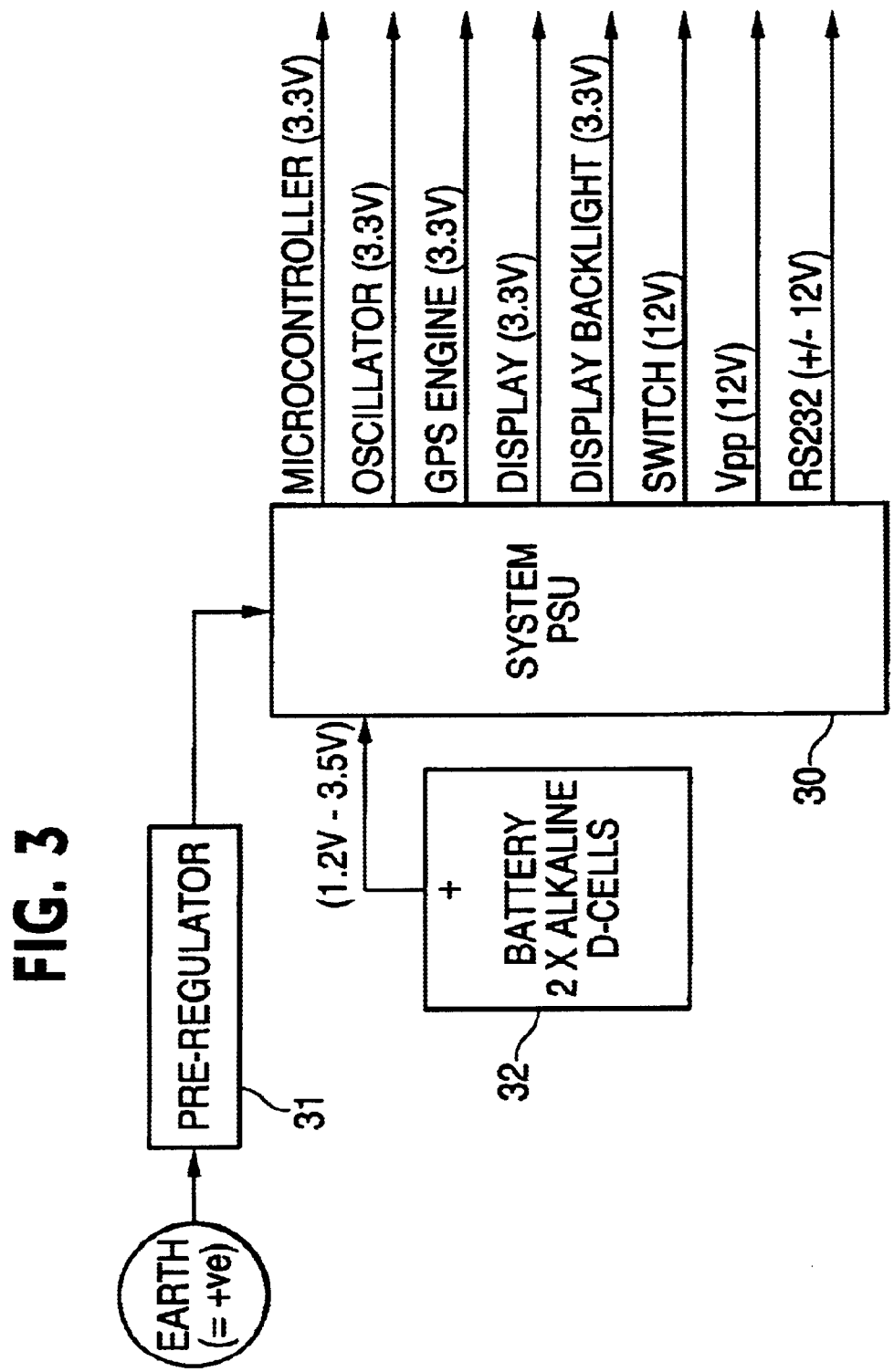
FIG. 3 shows the power supply of FIG. 1 in more detail.

FIG. 3 shows the power supply 17 in more detail. It comprises a power unit 30 which is connected to ground via a regulator 31, and is also connected to an independent power source 32 such as provided by a battery.

Suppose now that such interrupters are respectively connected to each of a plurality of pipes. The microprocessors 20 of each interrupter may then by programmed to apply a modulation to the cathodic protection voltage on the pipe, and so enable the pipe to be distinguished. The GPS unit 23 then acts as an independent synchroniser of the interrupters, since the signals which each provide to the corresponding microprocessor are synchronised, without the interrupters being physically interconnected.

Where multiple interrupters are used in this way, the modulations which each apply to the cathodic protection voltage of the respective pipes needs to be distinguishable.

Preferably, this is done by making the signals a sequence of binary levels, as represented by the open and closing of the switches. For multiple interrupters, the bit pattern thus defined by the switching is designed so that each pattern is orthogonal to all other patterns.

Orthogonality can be expressed mathematically as: $S1(t) \cdot S2(t)=0$ where S1 and S2 are the signal waveforms, represented as functions of time. The integral is taken over a period of time equal to the repeat period of the waveforms. If the equation holds true then the two signals $S1(t)$ and $S2(t)$ are orthogonal, provided neither signal is trivial, i.e. $S1^2(t)$ 0 and $S2^2(t)$ 0

Figure 4:
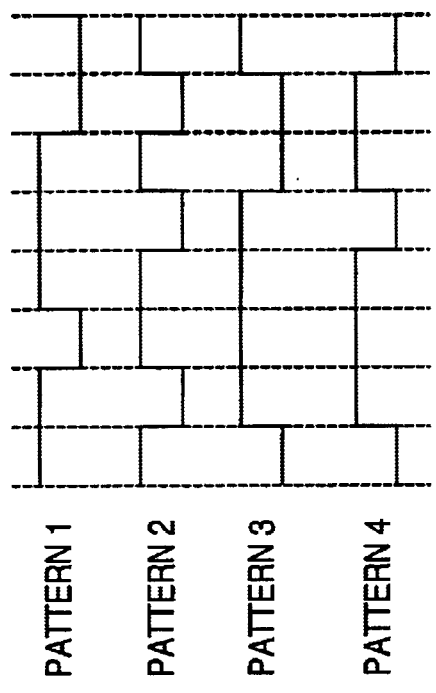
FIG. 4 illustrates orthogonal signal patterns that may be used with a series of interrupters.

FIG. 4 illustrates four orthogonal patterns. It can be noted that the aim of these patterns is to maximise the energy content of each pattern, while maintaining orthogonality. It would be possible to have single pulse of duration of an appropriate fraction of the cycle, but the total energy content of the pulses would then be limited. The technique of using orthogonality then means that the energy content can be increased while maintaining distinguishably.

In order for the signals to be orthogonal, they must be operating in a known phase relationship. In order for that to be possible, when the interrupters are turning on and off, the interrupters must be synchronised as previously mentioned. In general, it is not sufficient simply to synchronise the interrupters in the sense of providing them with an internal clock, and then allowing them to run free. Whilst it is possible to provide internal clocks with sufficient accuracy for this to be achieved, such clocks are not practical options because of their cost. However, if cheaper, and therefore less accurate clocks were used, synchronisation would be lost unless there was some external reference. Note it is also undesirable to interconnect the interrupters to achieve synchronisation.

Therefore, in this embodiment of the invention, a time (a pre-set time) is set which is which is known to all the interrupters. Then, whenever an interrupter is to start operation, it determines how long has passed between that pre-set time and the time it is to start, in terms of the number of cycles and part cycles of its signal, as if the signal had been operating continuously since the pre-set time. Then, the interrupter starts operating at which ever point in its cycle is thus determined. Thus, whenever an interrupter starts to operate it starts at which ever point in its cycle it would have reached if it had been operating continuously since the pre-set time.

Figure 5:
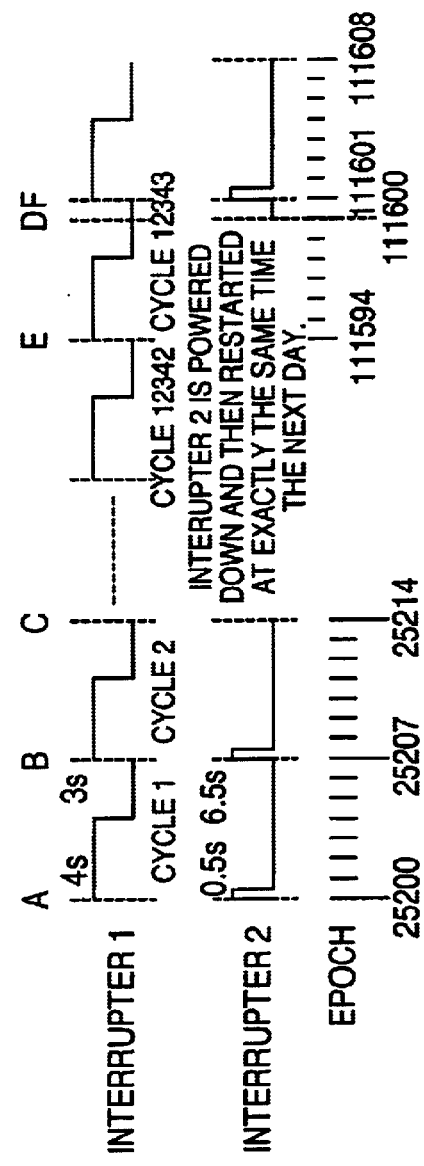
FIG. 5 illustrates the synchronisation of two orthogonal signal patterns.

This operation is illustrated in FIG. 5. In FIG. 5, the modulations of two interrupters are illustrated, both of which have a seven second cycle but one of which is on for 4 s and off for 3 s and the other of which is on for 0.5 s and off for 6.5 s. At a point A, both are synchronised. They remain synchronised at point D seven seconds later, but at point C the second interrupter is powered down. The first interrupter continues to operate. Next, supposes that both interrupters had been operating continuously for 25211 s at point A, and both had been synchronised for all that time, with the zero time then being the pre-set time referred to above.

Suppose now at point D, the second interrupter is to be turned back on. The second interrupter measures the time between point D and the pre-set time and, in the example shown in FIG. 5, it is determined that 111601 s has elapsed. That number is not divisible by seven, nevertheless the interrupter can determine at which point in its cycle is the start. It can determine that, if it had started its cycle at 111594 s after the arbitrary preset time (at point E) it would start in synchronisation with interrupter 1. However, in fact another 6 s has passed since point E. Thus, interrupter 2 is to start 6 s into its cycle, so that the on pulse occurs one second later at 111601 s being point F, at which point the second interrupter is again synchronised with first interrupter.

Thus, by determining the time from the pre-set time, determining the number of cycles and part cycles which have elapsed since then, and starting the interrupter signal at whichever point in the cycle is thus determined, the interrupter is able to re-synchronise itself with interrupters without having to be linked to those other interrupters.

In order to achieve this it is necessary for the interrupter to be able to determine how much time has elapsed since the pre-set time, but this can be obtained from GPS signals, derived e.g. from the GPS device 23 in FIG. 2, which signals carry time information. In the embodiment in FIG. 5, both signals have the same period 7(S) this technique can be applied to signals with different periods. Consider the case where one signal has a 7 second period and the other has a 9 second period. In such a case, the signals repeat together every 63 seconds. Nevertheless, if either interrupter is turned off, and then restarted, and it calculates the point in its cycle which it is to start, relative to the arbitrary pre-set time, then the interrupter which has been turned off and turned on will operate as if it had never been turned off, and thus will come back in synchronisation every 63 seconds in the same way as before.

Moreover, the signal need not be restricted necessarily to binary levels. The method described will work with arbitrary signals.

In the following description of the method of synchronisation the following symbols are used:

n the number of bits in a periodic signal,

T the period of a signal in seconds, r the bit rate of a signal in bits per second, i the bit number within a periodic signal in the range 0 to n−1, t the current one-second epoch as described above.

Since the signal to be transmitted is periodic, it must consist of a repeated sequence of n bits defined by $$n=rT$$

Two units will be synchronised correctly if at each instant they are in agreement about the current bit number, i within the signal. This is achieved by computing i at the commencement of each one-second epoch using this formula:

$$i=\text{remainder }[rt/n] \text{ where the } </= \text{ signifies integer division.}$$

The use of this formula together with the unique time information derived from GPS enables this synchronisation to be achieved. The signals from the previous example are used to show how this method succeeds where the other methods failed.

In many practical situations when locating a pipe, it is found that the current flowing along another underground service in the vicinity interferes with the signals on the pipe being investigated. In such a case the signals from the plurality of sensors in a detector may be used to indicate that the current is not flowing on a single service, as the signals do not follow the field pattern expected from a single conductor carrying the current. Using a locator indicator in these conditions may result in the incorrect location of the pipe as well as an incorrect current flow measurement.

Using the signals measured by many sensors, it is possible to determine the location of two or more pipes and the current flowing in them that give the field strengths that most closely match the signals measured.

The technique consists of two stages. Firstly the location of one of the pipes is determined, usually by isolating the current flowing on it and hence locating it correctly. Then the pipe is returned to being non-isolated, thus having the same interfering signal current as is on the adjacent pipe. The signal strengths at the sensors is then measured and using the information of the location of one of the pipes the location of the other is found along with the current flowing on both. This is done using a mathematical model of the fields generated by the pipes. The fields that would be generated by a pipe at the known pipe location are removed from the measured signals, and by varying the current on this pipe in the model the best fit to the measured signals is found. The model is optimised to give a best fit to the fields for a single additional pipe at an unknown location and having optimised this location the currents on both pipes are calculated from the fields from each pipe.

Having accurately measured the signals from each of the sensors, the position of the pipe can be determined. Having done this it is then possible to decide whether the signals are correct for there being one pipe or whether there are two pipes in the same vicinity. In the former case the calculated position will be correct. In the latter the position will not be the correct location of either pipe. In this case the location of one pipe should be measured either by ensuring that a signal current flows only on one pipe to make an accurate measurement or by some other means. Having determined the location of one pipe the position of this can be used to eliminate the field that this pipe would generate in the more complicated case with the two pipes. In this way the current on both pipes and the location of the second pipe may be determined.

It is not always possible to eliminate the effect of interference of one pipe on another by considering multiple modulation expressed above. In some situations, it is not possible to modulate the pipes differently. Moreover, in other situations, signals on one pipe couple to another pipe, and in that case the two signals have the same modulation (because they have common origin) and so cannot be eliminated by the processing described above. Nevertheless, it is still possible to minimise the effect of an interfering pipe.

Figure 6:
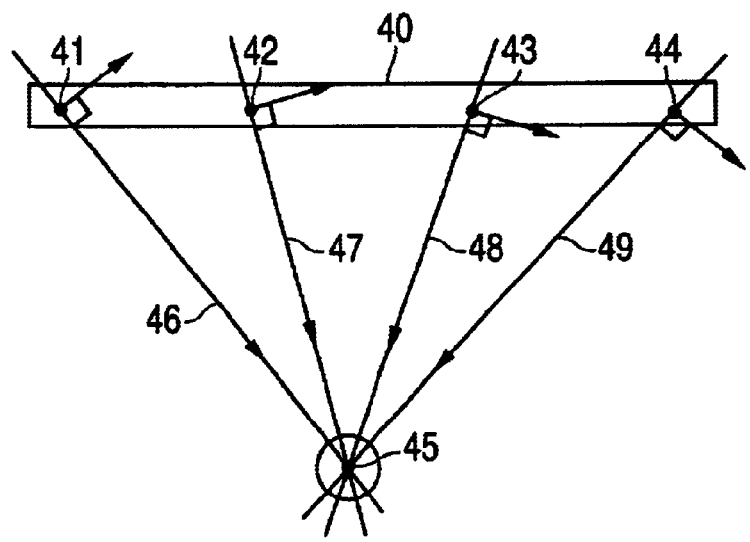
FIG. 6 shows the location of a pipe using a detector with several sensors.

FIG. 6 illustrates a detector detecting the location of a pipe in the situation where there is no interference. The detector 40 has multiple sensors 41, 42, 43, 44 thereon, spaced along the length of the detector at known intervals, and each detect the magnetic fields due to the signals on the pipe 45. The sensors 41 to 44 will detect maximum field strength in directions which intersect at the pipe 45, as illustrated by arrows 46 to 49. Thus, in the absence of interference, the position of the pipe 45 can be determined accurately.

It should be noted that the sensor described with reference to FIG. 6 is illustrated in more detail in WO98/54601 thus its detailed structure, control, signal processing, etc will not be described in more detail now.

Figure 7:
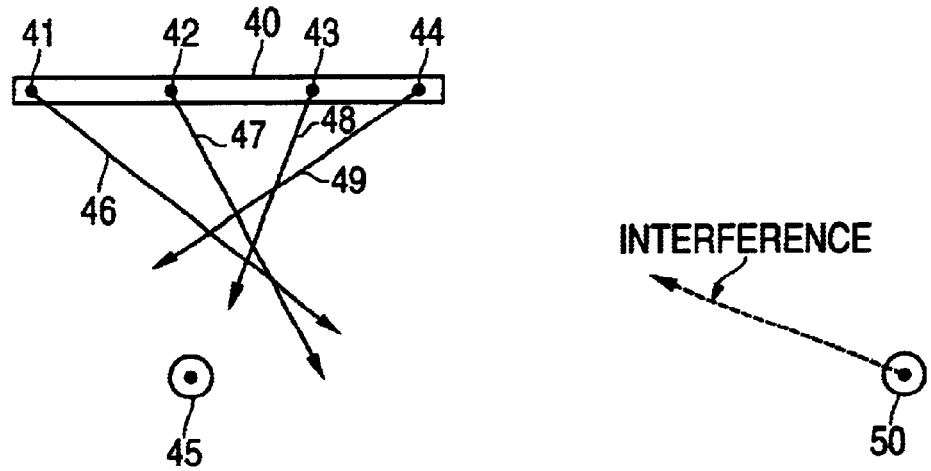
FIG. 7 is similar to FIG. 6, but shows the effect of interference due to a second pipe.

FIG. 7 illustrates the situation when there is a second pipe 50 carrying a current which generates an magnetic field which interferes with the field from the first pipe 45 at the sensors 41 to 44. In this case, the directions of maximum field represented by arrows 46 to 49 do not coincide at the pipe 45. Indeed, as illustrated in FIG. 7, they do not have a meaningful coincidence at all. The position of the first pipe 45 is thus impossible to determine.

Figure 8:
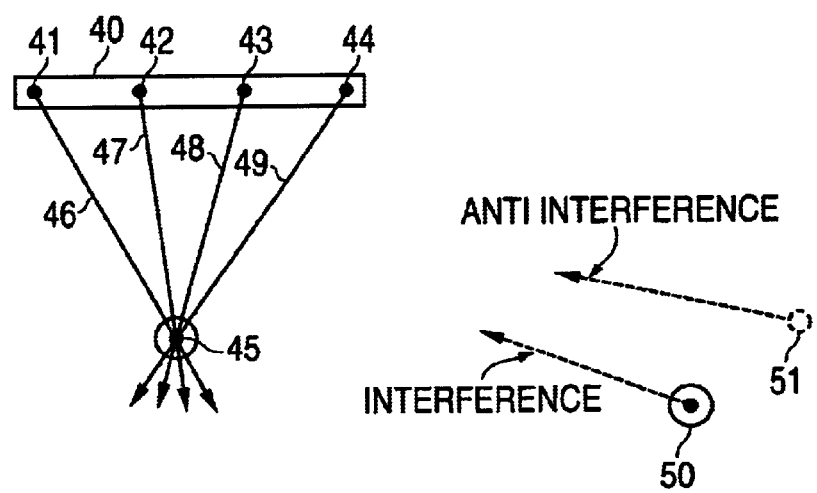
FIG. 8 is similar to FIGS. 5 and 6, but shows the effect of Aanti-interference@.

Suppose now that a "virtual" pipe is assumed to exist at point 51 shown in FIG. 8, carrying a current. Pipe 51 can itself be considered to generate magnetic fields which would interfere with the signals received with the sensors 41 to 44 due to the pipe 45, and by varying the current in pipe 51 it can generate an Anti interference effect which has the effect of cancelling the interference due to pipe 50, so that the arrows 46 to 49 representing the maximum field strength detected by the sensors 41 to 44 then coincide (or substantially coincide) at the pipe 45. Thus, by varying the current in pipe 51 until a best fit is obtained for the arrows 46 to 49, the location of the pipe 45 can be determined with sufficient accuracy for practical purposes.

Of course, pipe 51 will not normally be a real pipe. Instead, the signals from the sensors 41 to 44 are modified as if there was a pipe at point 51, and the virtual current in that virtual pipe varied until the best fit was obtained. It has been found that the accuracy of this arrangement does not require the location of the virtual pipe 51 to coincide with the pipe 50. The interference effect is largely position independent. Therefore, it is possible for the user to estimate a suitable position for the pipe 51 or indeed for the detector to use a pre-set position. A suitable current value can be found at which the pipe 51 cancels the pipe 50.

FIG. 8 assumes that the pipes 50,51 are on the same side of the first pipe 45. Whilst reasonable results can be obtained even when they are on opposite sides of the first pipe 45, it may be better to try for a best fit with the pipe 51 on one side of the first pipe 45, and then to repeat the process with the pipe 51 on the other side of the first pipe 45, to see which produces the "better" best fit. Note that in practical situations, it is usually possible to say whether the interfering pipe is on one side or other of the pipe 45 to be investigated.

This technique can be used to eliminate the effect of multiple interfering pipes. Magnetic fields received at the sensors 41 to 44 of any pair (or more) of pipes is usually directly equivalent to the magnetic field received by a single pipe at some intermediate location. The composite effect created by that single pipe can then be cancelled by providing a virtual pipe equivalent to pipe 51 shown in FIG. 8.

Figure 9:
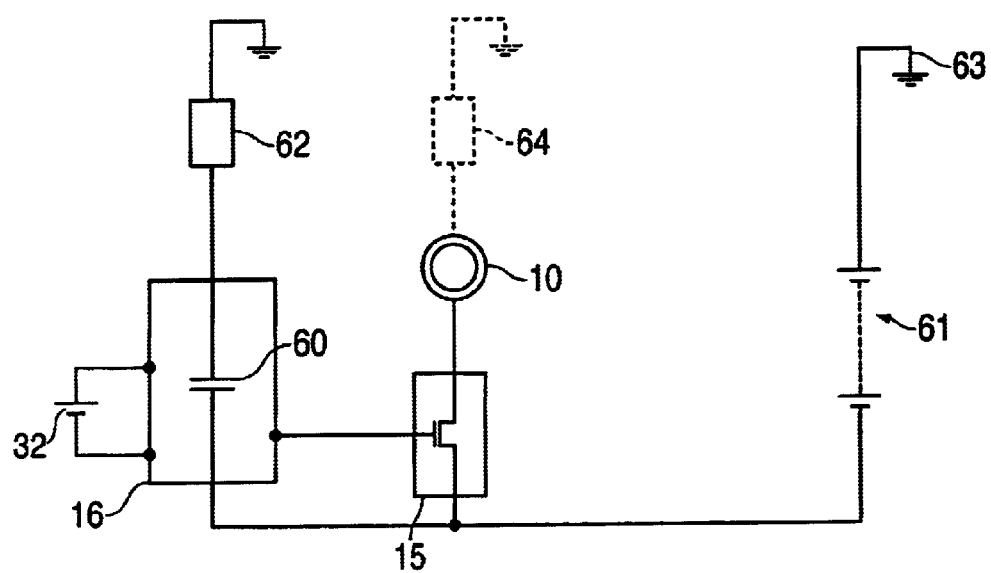
FIG. 9 shows a power arrangement that may be used with an interrupter of the present invention.

It was previously mentioned, with reference to FIG. 3, the power supply 17 into FIG. 1 may comprise of power unit 30 and an independent power source 32 such as provided by a battery. However, it is also possible to provide power to the control unit 16 in an other way, as illustrated in FIG. 9. Control unit 16 may still have the power source 32, to provide a backup, but in the arrangement shown in FIG. 9 this is not the main source of power. Instead, the controller contains a capacitor 60 (other parts of the control unit 16 are not shown in FIG. 9) which is connected between a terminal of the cathodic protection voltage supply 61 and ground via a resistor 62. The other end of the cathodic protection voltage supply 61 is also connected to ground as shown at 63, and the pipe 10 maybe considered also connected to ground via a resistor 64. It will be appreciated that the resister 64 is not a separate component, but is created due to the nature of the materials surrounding the pipe 10. When the interrupter switch 15 is on, the cathodic protection voltage is supplied from the power supply 51 to the pipe 10. However, since the capacitor 60 is also connected to the cathodic protection voltage supply 61, the voltage is established across it causes charge to be stored which with current flowing through the existing 62) and thus the power represented by that store charge may be used to power the control unit 16 when the interrupter switch 16 needs to be turned off. Then using a solid state switch, such as a power FET, the energy needed to switch the switch 15 is minimised, and thus there will be sufficient power stored in the capacitor 60 to achieve the effect required.

Hence, it is possible to use the cathodic protection power supply to power the control unit for the interrupter. It can also be appreciated that the techniques envisaged in FIG. 9 can be applied to control of other devices connected to the pipe to which a cathodic protection voltage is applied.

What is claimed is:

1. An interrupter for controlling the negative protection voltage applied to an underground pipe or cable, the interrupter comprising:

a switch for controlling said protection voltage;

means for storing a predetermined fixed prior time;

means for storing a predetermined modulation cycle, the predetermined modulation cycle having its origin at the fixed prior time;

timing means for determining the time elapsed between said fixed prior time and the current time;

means for determining the location within said modulation cycle at the current time;

means for setting a signal to a value corresponding to the determined location with said modulation cycle, and subsequently modulating said signal according to said modulation cycle; and control means for controlling said switch and modulating said negative protection voltage according to said modulated signal.

2. An interrupter according to claim 1, wherein said timing means comprises a GPS receiver.

\* \* \* \* \*